United States Patent
Lin

(10) Patent No.: US 9,023,106 B2
(45) Date of Patent: *May 5, 2015

(54) MEDICAL IMPLANT

(75) Inventor: Chih I Lin, Taipei (TW)

(73) Assignee: Spirit Spine Holdings Corporation, Inc., Pasadena, CA (US)

( * ) Notice: Subject to any disclaimer, the term of this patent is extended or adjusted under 35 U.S.C. 154(b) by 376 days.

This patent is subject to a terminal disclaimer.

(21) Appl. No.: 13/608,323

(22) Filed: Sep. 10, 2012

(65) Prior Publication Data

US 2013/0006197 A1 Jan. 3, 2013

Related U.S. Application Data

(63) Continuation of application No. 12/848,270, filed on Aug. 2, 2010, now Pat. No. 8,377,131, which is a continuation-in-part of application No. 11/808,026, filed on Jun. 6, 2007, now abandoned.

(51) Int. Cl.
*A61F 2/44* (2006.01)
*A61B 17/70* (2006.01)

(52) U.S. Cl.
CPC ............. *A61B 17/7097* (2013.01); *A61F 2/441* (2013.01); *A61F 2002/4495* (2013.01)

(58) Field of Classification Search
CPC ................ A61B 17/7097; A61F 2/441; A61F 2002/4495

USPC ........................................................ 623/17.12
See application file for complete search history.

(56) References Cited

U.S. PATENT DOCUMENTS

| | | | |
|---|---|---|---|
| 6,719,773 B1 | 4/2004 | Boucher et al. | |
| 8,377,131 B2 * | 2/2013 | Lin ............................. | 623/17.12 |
| 2004/0220615 A1 | 11/2004 | Lin et al. | |
| 2005/0049604 A1 | 3/2005 | Singer et al. | |
| 2007/0276491 A1 * | 11/2007 | Ahrens et al. .............. | 623/17.11 |

* cited by examiner

*Primary Examiner* — Yashita Sharma
*Assistant Examiner* — Megan Wolf
(74) *Attorney, Agent, or Firm* — Bacon & Thomas, PLLC

(57) ABSTRACT

A medical implant includes a flexible container having two layers of flexible surrounding walls, each surrounding wall being provided with a plurality of through holes; a tubular fitting being connected to an open end of the flexible container for inserting or infusing a medical filling material into the flexible container through the tubular fitting; and a thrust part connected to the flexible surrounding walls of the flexible container and at a distal end of the flexible container. The thrust part has a receiving seat and a ring, the receiving seat having a central bore and an annular groove surrounding the central bore and opposite to the central bore, wherein a tubular surrounding wall is inserted into the ring and is folded so that the two layers of flexible surrounding walls are formed with the ring imbedded between the two layers of flexible surrounding walls, and the ring with the two layers of flexible surrounding walls are received in the annular groove and detained therein due to friction.

9 Claims, 16 Drawing Sheets

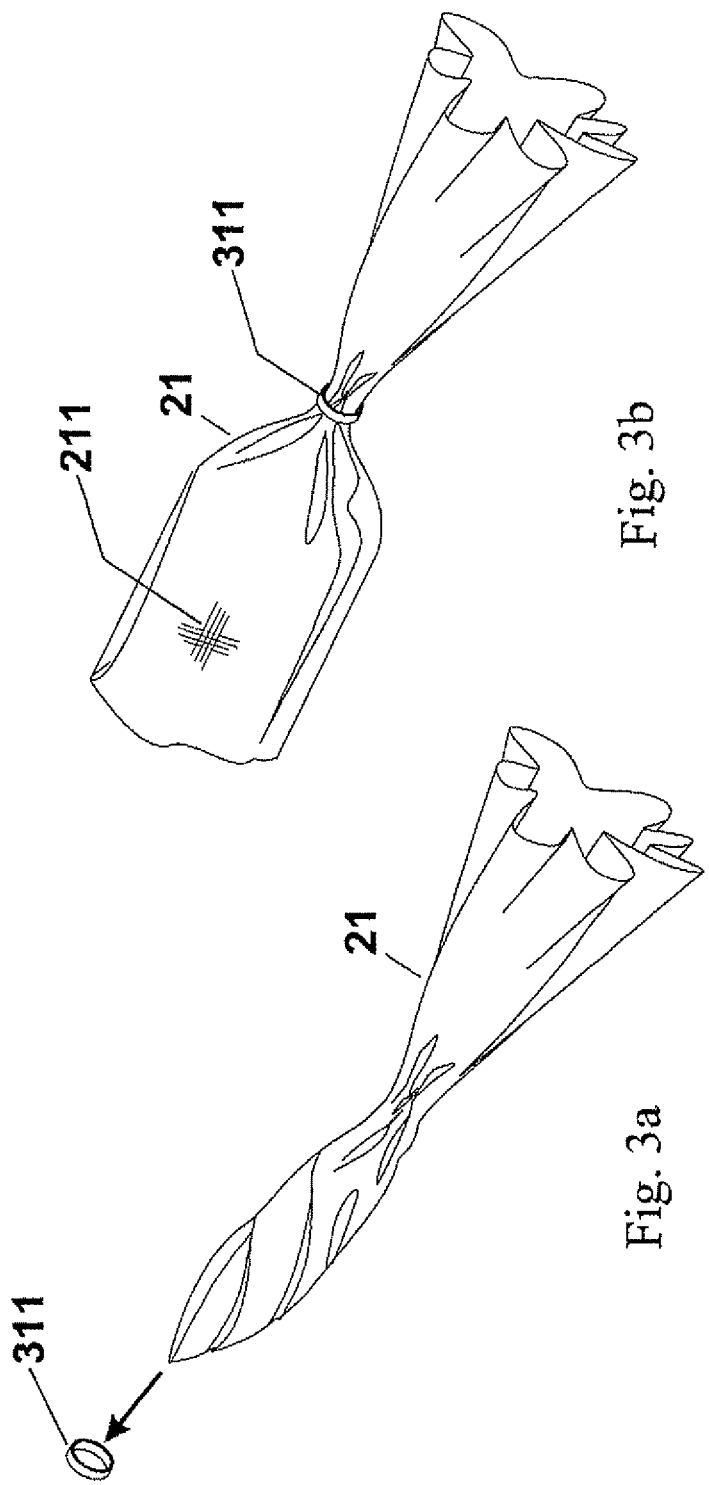

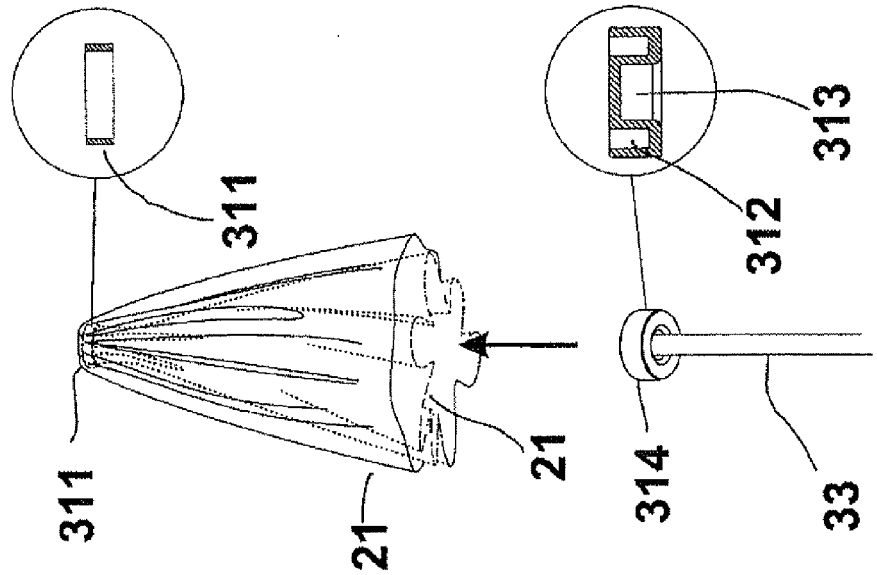
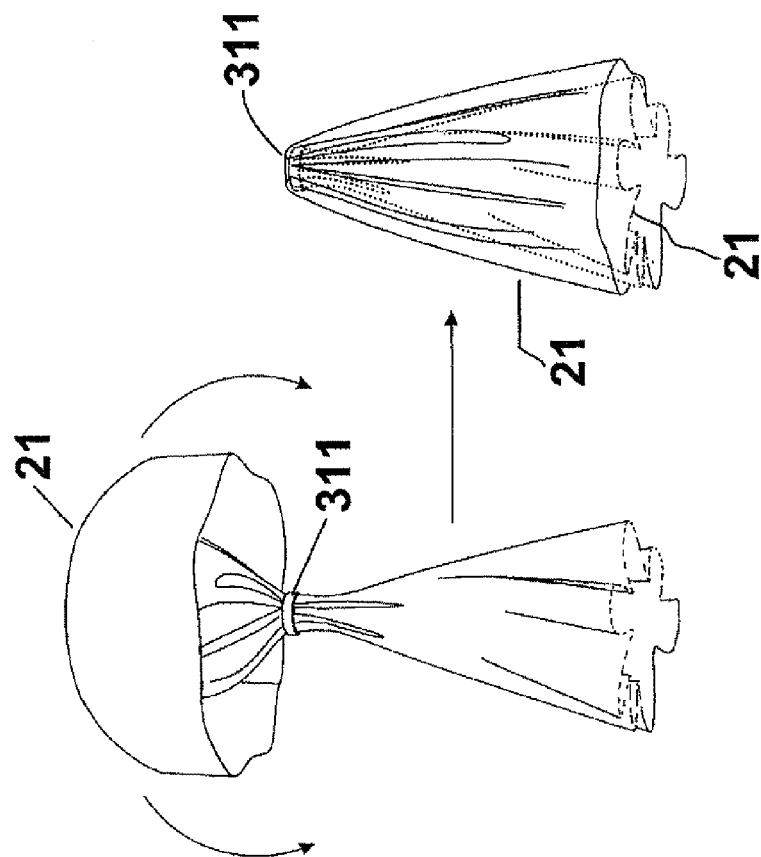
Fig. 3c
Fig. 3d

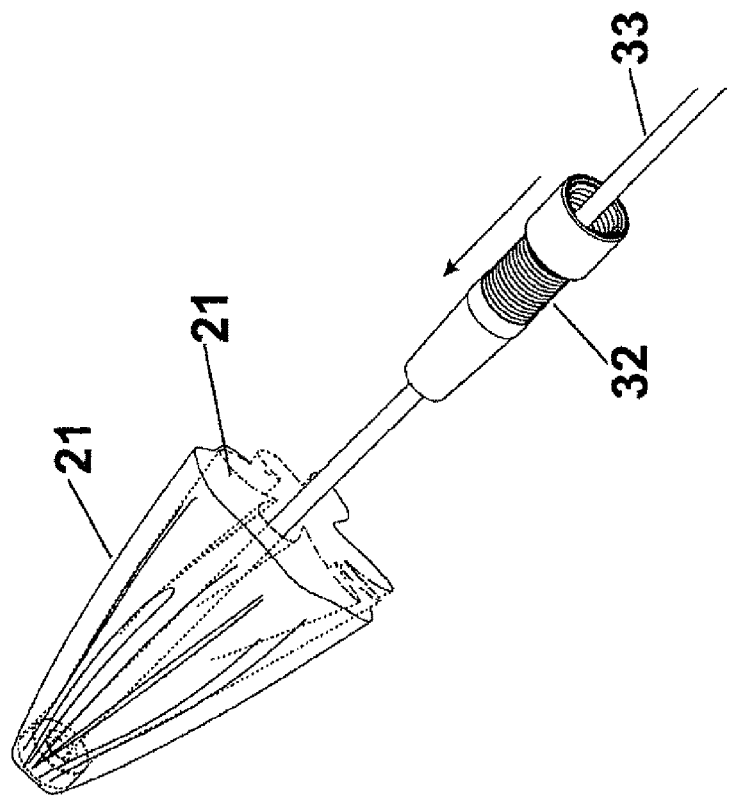
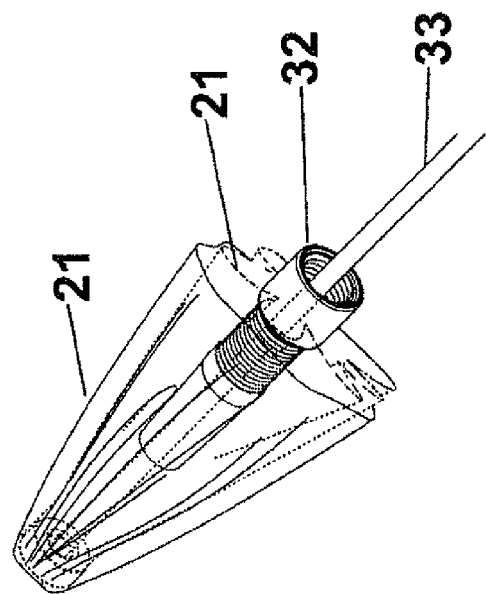
Fig. 3f
Fig. 3g

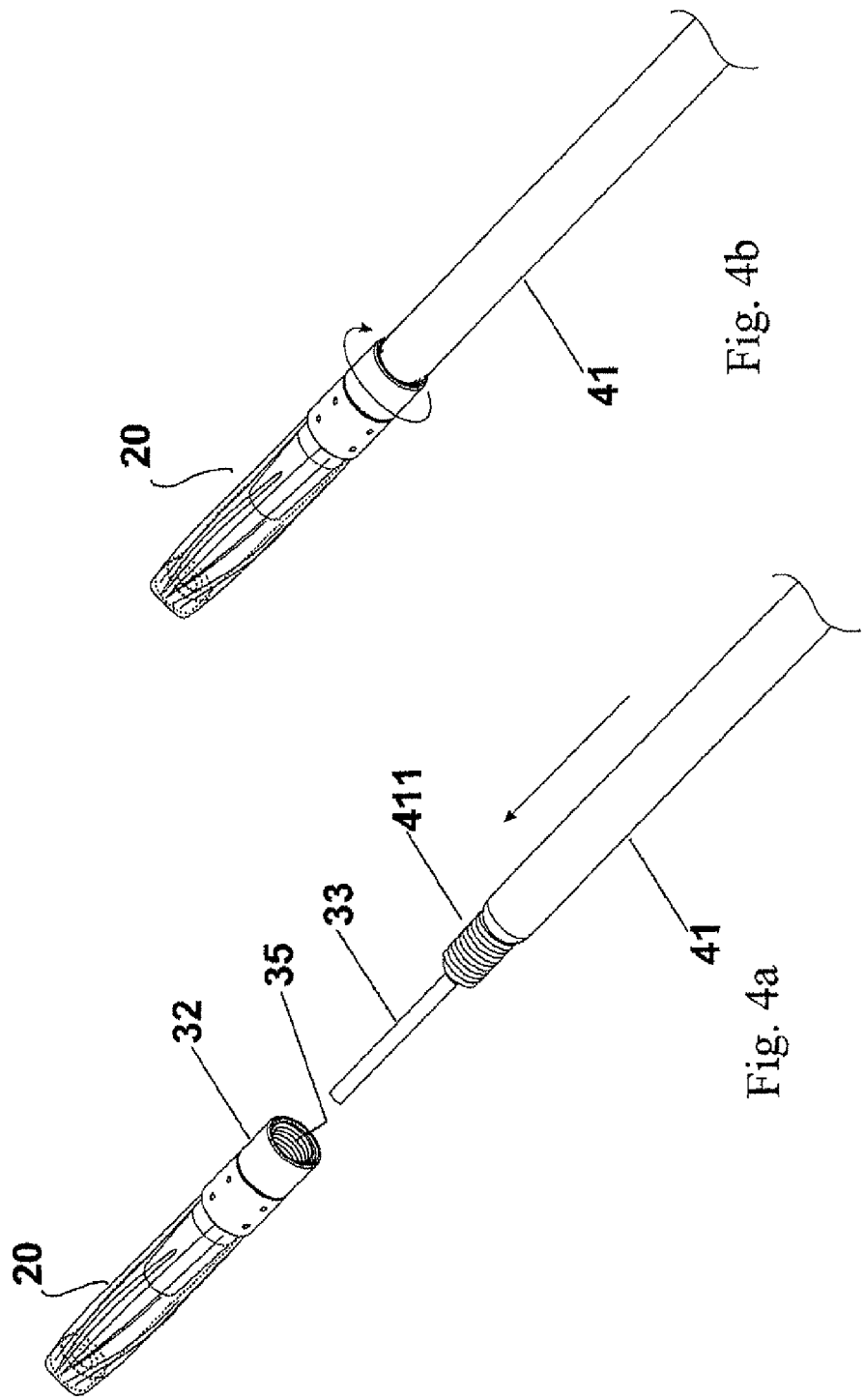

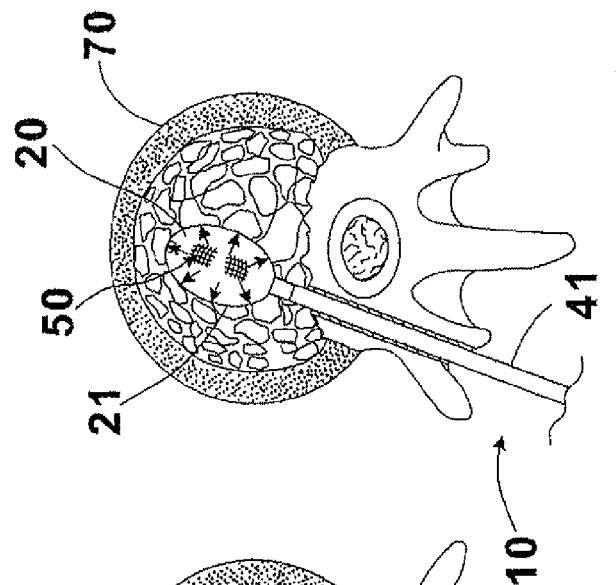
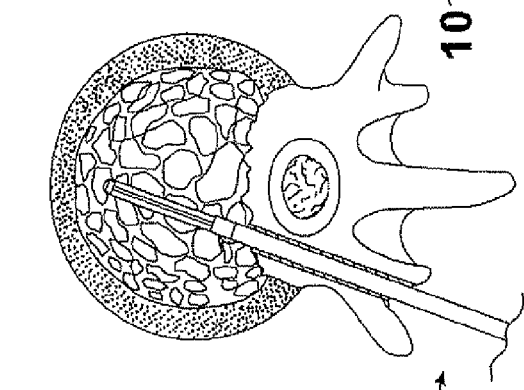
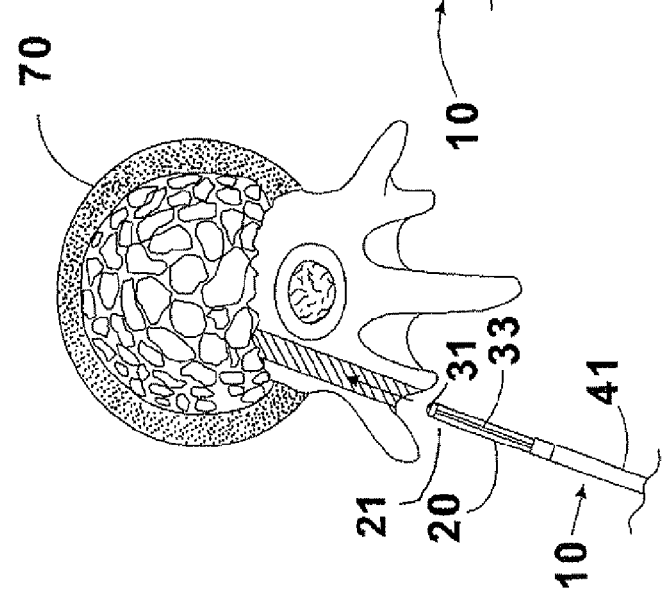
Fig. 4e
Fig. 4d
Fig. 4c

MEDICAL IMPLANT

CROSS-REFERENCE TO RELATED APPLICATION

The present application is a continuation application of U.S. application Ser. No. 12/848,270, filed Aug. 2, 2010, which is a continuation-in-part application of U.S. patent application Ser. No. 11/808,026, filed Jun. 6, 2007, now abandoned, the entire contents of which are incorporated herein by reference.

FIELD OF THE INVENTION

The present invention is related to a medical implant, and particularly to a medical implant with a flexible container combined with a thrust part.

BACKGROUND OF THE INVENTION

U.S. Pat. No. 6,719,773 discloses an expandable structure for deployment in interior body regions, in which a complicated wrapping-deploying mechanism (legend 56 in FIGS. 3, 5, 6, 9, 10-17 of U.S. Pat. No. 6,719,773) is needed to insert the expandable structure into the vertebra body through a channel pre-formed. First, the structure is wrapped into a wrapped condition to facilitate the insertion of the structure into the vertebra body through the channel, avoiding the structure from being stuck in the channel. Next, the wrapping-deploying mechanism is used to restore the structure to its original shape for carrying out subsequent steps. Please refer to FIGS. 9-12 and related description in U.S. Pat. No. 6,719,773 for details.

US patent publication Nos. 2004/0073308 and 2006/0149379 disclose a porous mesh device without a wrapping-deploying mechanism. However, in order to avoid the expandable porous mesh device from being stuck in the channel, obstructing the performance of the subsequent steps, a cavity needs to be created in advance in the vertebral body (referring to FIGS. 2-15 of the two publications), the femoral head (referring to FIG. 16-18 of the two publications), or the tibia plateau (referring to FIG. 19-21 of the two publication), thereby the porous mesh device can be pushed forward after being stuck in the channel. Thus, the porous mesh device is deployed in the cavity and then retracted to a pre-determined position, thereby completing a deploying step of the porous mesh device. Since the application of this porous mesh device needs to create a cavity in a bone under treatment, the operation time is lengthened and the recovery time after operation is prolonged, as well.

SUMMARY OF THE INVENTION

An objective of the present invention is to provide a medical implant equipped with a thrust part.

Another objective of the present invention is to provide a medical implant which can be implanted without the need of creating a cavity in advance in a bone under treatment.

Still a further objective of the present invention is to provide a vertebral implant equipped with a thrust part.

Still another objective of the present invention is to provide a vertebral implant that can be implanted without the need of creating a cavity in advance in the vertebral body under treatment.

In order to accomplished the aforesaid objectives a medical implant constructed according to the present invention comprises:

a flexible container, a proximal end thereof being an open end, said flexible container having 2n layers of flexible surrounding walls, each surrounding wall being provided with a plurality of through holes thereon through which an interior of the flexible container is in fluid communication with an exterior of the flexible container, wherein n is an integer of 1-5;

a tubular fitting being connected to the open end of the flexible container for inserting or infusing a medical filling material into the flexible container through the tubular fitting; and a thrust part connected to the flexible surrounding walls of the flexible container and at a distal end of the flexible container, wherein the thrust part comprises a receiving seat and a ring, said receiving seat comprising a central bore and an annular groove surrounding the central bore and opposite to the central bore, wherein n layer of tubular surrounding walls is inserted into the ring and is folded so that the 2n layers of flexible surrounding walls are formed with the ring imbedded between the 2n layers of flexible surrounding walls, and the ring with the 2n layers of flexible surrounding walls are tightly received in the annular groove and detained therein, wherein n is defined as above. Preferably, n is 1.

The above-mentioned flexible container can be a flexible non-airtight filling member defined in the related inventions disclosed in US patent publication Nos. 2004/0122455, and 2004/0210297. Such a flexible container can also be a flexible container described in the similar devices disclosed in, for examples the above-mentioned US patent/publications: US patent publication Nos. 2004/0073308, and 2006/0149379; and U.S. Pat. No. 6,719,773. The definitions and usages of the surrounding walks) and through holes of the flexible container can also be referred to the inventions disclosed in US patent publication Nos. 2004/0122455, and 2004/0210297 and the related inventions, e.g. US patent publication Nos. 2004/0073308, and 2006/0149379; and U.S. Pat. No. 6,719,773.

The above-mentioned tubular fitting can be found in the related inventions disclosed in US patent publication Nos. 2004/0122455, and 2004/0210297. Such a tubular fitting can also be a tubular fitting described in the similar devices disclosed in, for examples the above-mentioned US patent/publications: US patent publication Nos. 2004/0073308, and 2006/0149379; and U.S. Pat. No. 6,719,773.

The above-mentioned flexible container and tubular fitting can be assembled by a technique described in the related inventions, or similar techniques described in, for examples the above-mentioned US patent/publications: US patent publication Nos. 2004/0073308, and 2006/0149379; and U.S. Pat. No. 6,719,773.

The above-mentioned medical filling material can be a medical material defined in the related inventions disclosed in US patent publication Nos. 2004/0122455, and 2004/0210297; or a medical filling described in similar techniques, e.g. the above-mentioned US patent/publications: US patent publication Nos. 2004/0073308, and 2006/0149379; and U.S. Pat. No. 6,719,773. That is the medical filling material of the invention is a slurry prepared prior to operation, which then solidifies after implantation, or a bone graft in the form of solid granules.

The present invention further provides a medical kit comprising the medical implant of the present invention and an infusion tool, said infusion tool comprising:

an infusion tube; and a syringe, in which one end of the infusion tube is provided with external threads which are threadably connected to inner threads provided at a proximal end of the tubular fitting, and another end of the infusion tube is connected to said syringe, so that the infusion tube and the flexible container are in fluid communication with each other, and so that a medical filling material as a slurry in the syringe can be pushed and squeezed into the flexible container.

Preferably, the medical kit further comprises a thrust pin received in the flexible container and the tubular fitting, in which a distal end of the thrust pin is received in the central bore of the receiving seat of the thrust part to tension the flexible surrounding walls of the flexible container.

The inventor of the present application uses a simple thrust structure to replace the complicated wrapping-deploying mechanism used in U.S. Pat. No. 6,719,773 and eliminate the wrapping-deploying step of the operation method in U.S. Pat. No. 6,719,773. Meanwhile, unlike US patent publication 2004/0073308, the present invention does not need to crate a cavity in advance in the bone under treatment, and does not need to perform a deploying step required in the prior art. Furthermore, when necessary, the step of creating a channel in the bone under treatment can be omitted. Such a step of creating a channel is a necessary step in a similar operation according to the current technology. Thus, the medical implant according to the invention can simplify the operation procedures and achieve the advantages of shortening the operation time and providing faster recovery after operation.

BRIEF DESCRIPTION OF THE DRAWINGS

FIGS. 3a to 3j are schematic perspective diagrams showing the procedures of assembling a medical implant according to a preferred embodiment of the present invention.

FIGS. 4a to 4b are schematic perspective diagrams showing the procedures of assembling a medical kit using the medical implant shown in FIG. 3j.

FIG. 4c to 4e are schematic diagrams showing operation procedures for implanting the medical implant of the present invention into a vertebral body.

DETAILED DESCRIPTION OF THE INVENTION

Figure 1A:
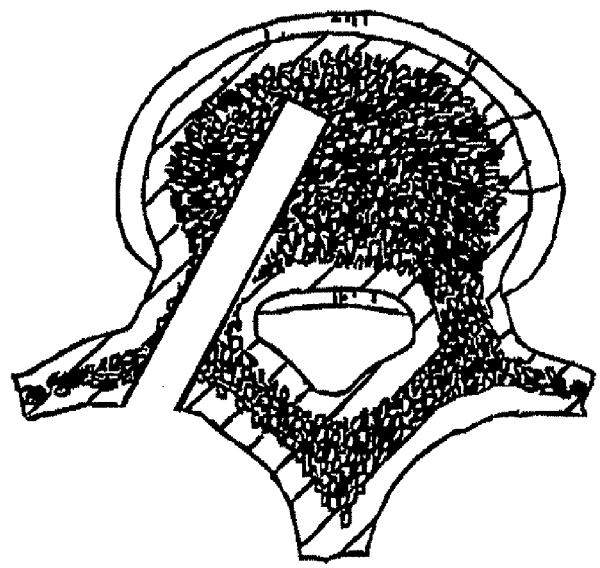
FIG. 1a to FIG. 1j are schematic diagrams showing operation methods using a porous mesh device described in the prior art US patent/patent publications, wherein FIGS. 1a and 1h use a pre-formed cavity and FIGS. 1i to 1j use a pre-formed channel in the vertebral body.
Figure 1B:
Figure 1C:
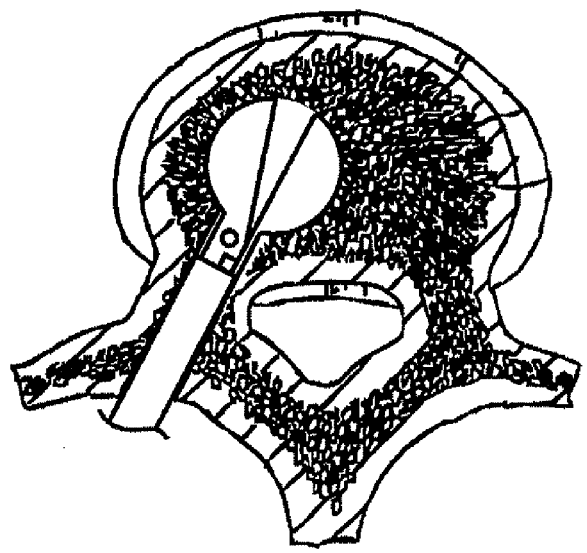
Figure 1D:
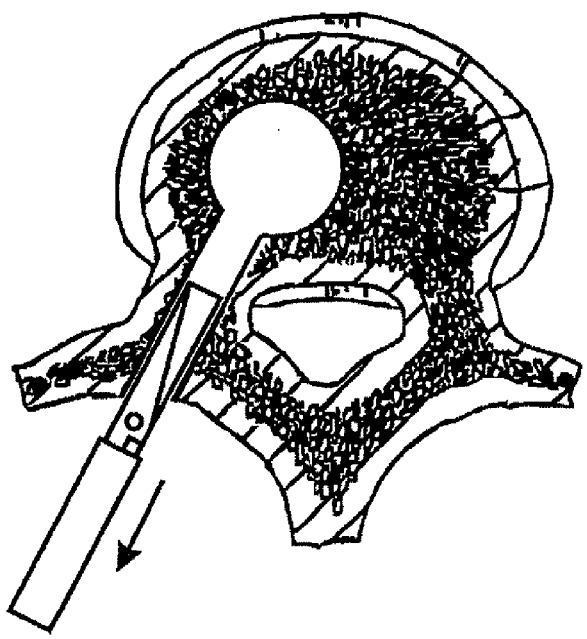
Figure 1E:
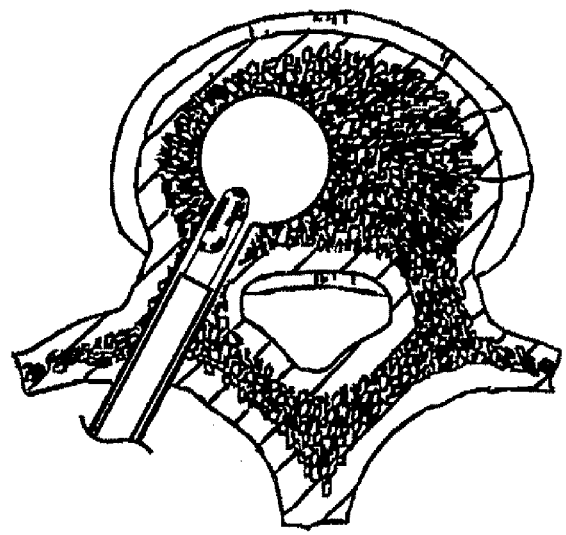
Figure 1F:
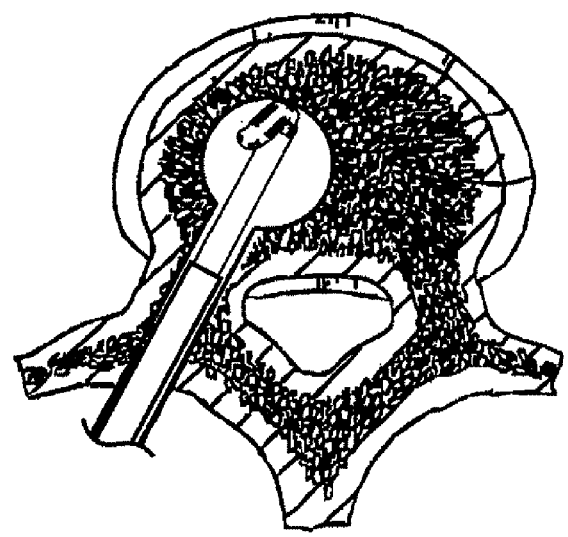
Figure 1G:
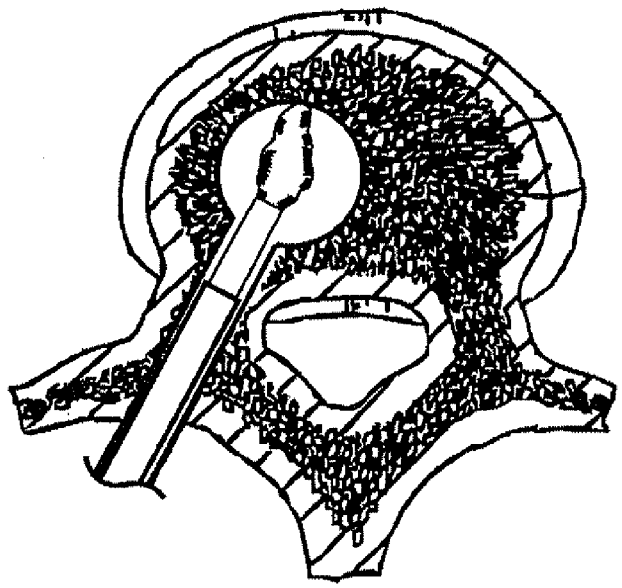
Figure 1H:
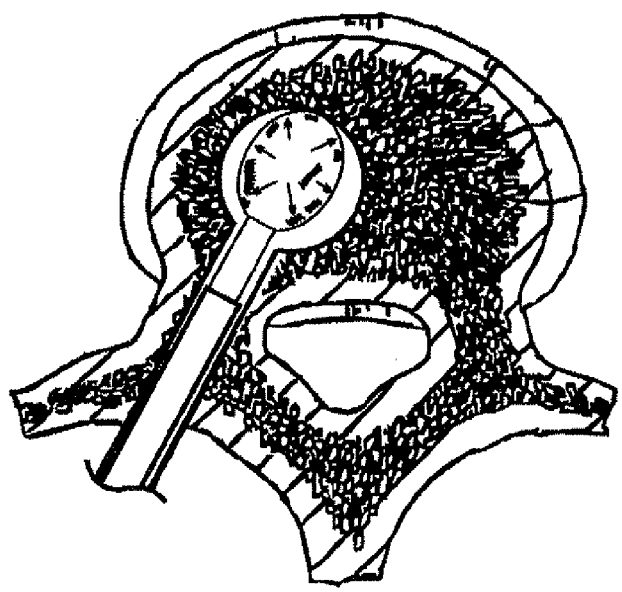
Figure 1I:
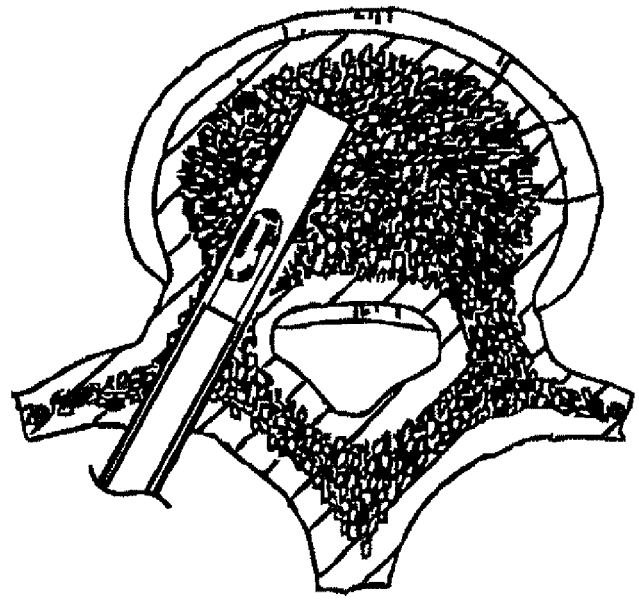
Figure 1J:
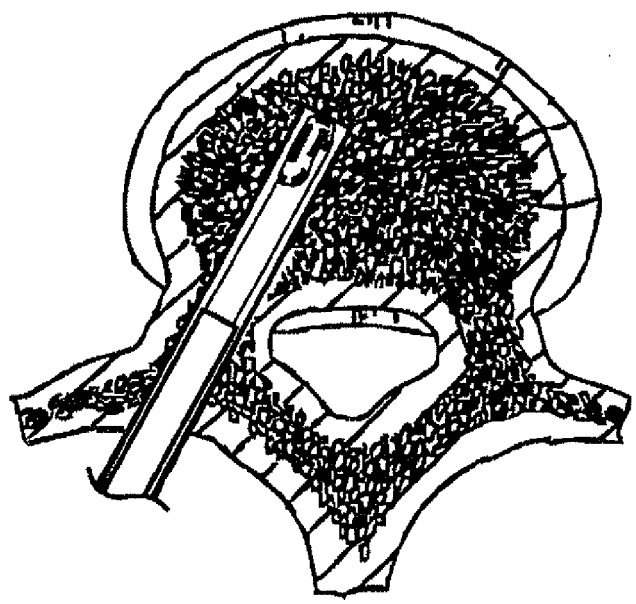

Preferred embodiments of the present invention in conjunction with the accompanying drawings will be described in the following to further elaborate the present invention:

FIG. 1a to FIG. 1d show that a cavity needed to be created in the vertebral body in advance for the porous mesh device disclosed in US patent publication Nos. 2004/0073308 and 2006/0149379 to be successfully deployed in the vertebral body. FIG. 1e to FIG. 1h show that after a cavity was created, the porous mesh device is pushed to a pre-determined position (FIG. 1e), and then the pushing is continued until the porous mesh device hits the bottom of the cavity (FIG. 1f). Next, the porous mesh device is retreated to a pre-determined position (FIG. 1g), and then the porous mesh device in the cavity of the vertebral body is deployed (FIG. 1h). In U.S. Pat. No. 6,719,773 a complicated wrapping-deploying mechanism is inserted into the vertebra body through a channel pre-formed (FIG. 1i). Next, the wrapping-deploying mechanism is pushed to hit the bottom of the pre-formed channel (FIG. 1h), and then is retreated to a predetermined position prior to restoring its original shape.

Figure 2:
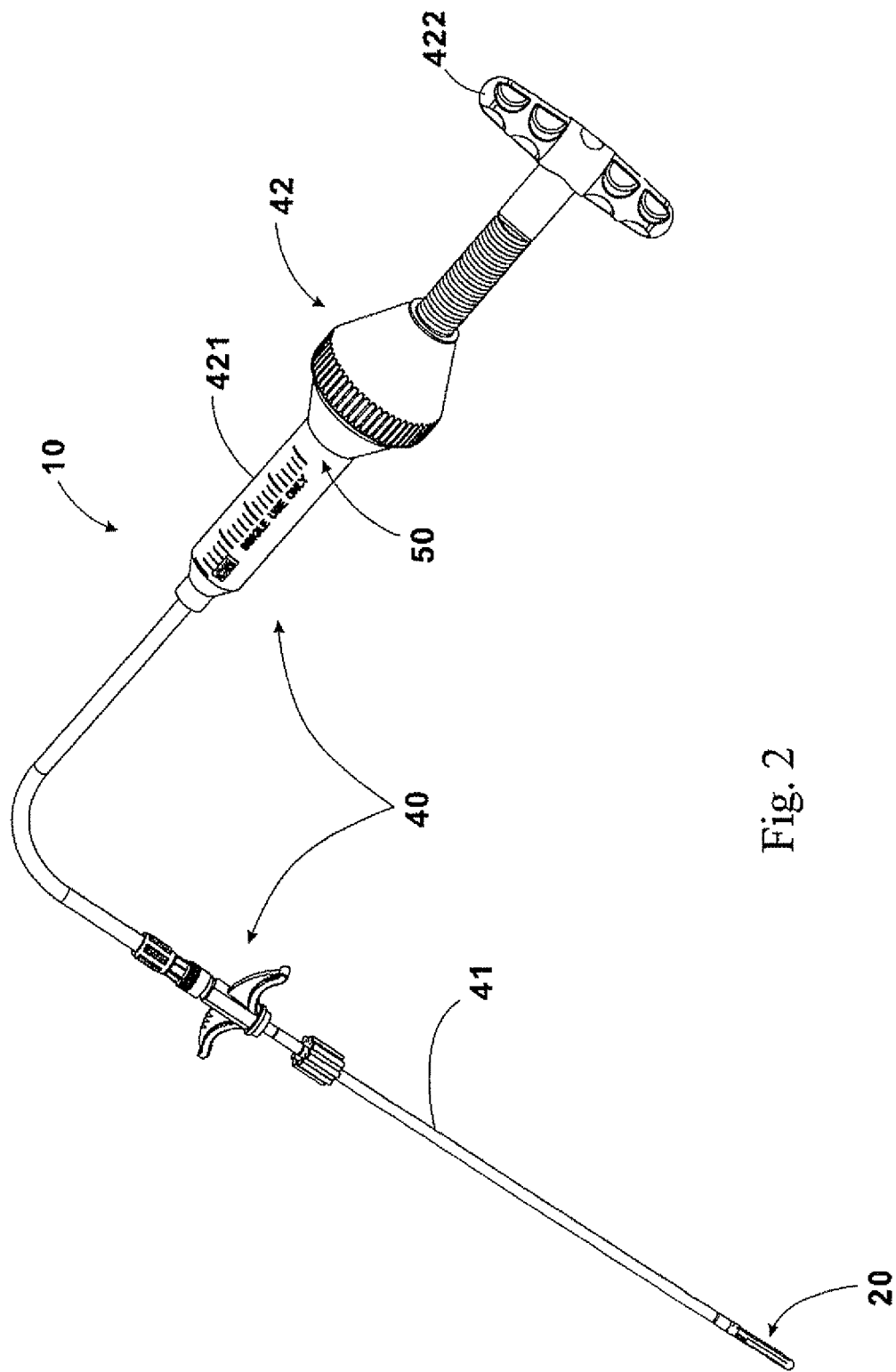
FIG. 2 is a schematic perspective diagram showing a flexible non-airtight medical filling device (a medical kit) according to a preferred embodiment of the present invention.

FIG. 2 shows a flexible non-airtight medical filling device 10, i.e. the above-mentioned medical kit of the present invention, which includes: a flexible non-airtight filling member 20 (i.e. the medical implant) and a matching infusion tool 40. The infusion tool 40 includes an infusion tube 41, a syringe 42, and a medical filling material 50 which is prepared into a slurry form and loaded in the syringe 42.

Referring to FIG. 2, FIGS. 4a and 4b, one end of the infusion tube 41 is provided with a plurality of external threads 411 corresponding to a plurality of threads 35 on the inner wall of a nozzle 32, and they are threadably connected, communicating the infusion tube 41 with a housing in the medical implant 20. Another end of the infusion tube 41 is connected to the syringe 42. The syringe 42 includes a housing cylinder 421 and a push rod 422. The housing cylinder 421 is able to store the slurry medical filling material 50, and the push rod 422 is used to squeeze the slurry medical filling material 50 into the housing of the medical implant 20 through the infusion tube 41.

FIG. 2 and FIGS. 4a and 4b shows the inventions disclosed in the parent application, U.S. patent application Ser. No. 11/808,026, filed Jun. 6, 2007. In the following we will describe the improvements disclosed in this continuation application.

FIGS. 3a to 3i show the procedures of assembling the medical implant 20 of the present invention. The medical implant 20 as shown in FIG. 3j has a flexible container 29, said flexible container having two layers of flexible surrounding walls 21, each surrounding wall being provided with a plurality of through holes (not shown in FIG. 3j) thereon through which an interior of the flexible container is in fluid communication with an exterior of the flexible container 29; a tubular fitting 39 being connected to an open end of the flexible container 29 for inserting or infusing a medical filling material into the flexible container through the tubular fitting; and a thrust part 31 connected to the flexible surrounding walls 21 of the flexible container 29 and at a distal end of the flexible container 29.

Figure 3E:
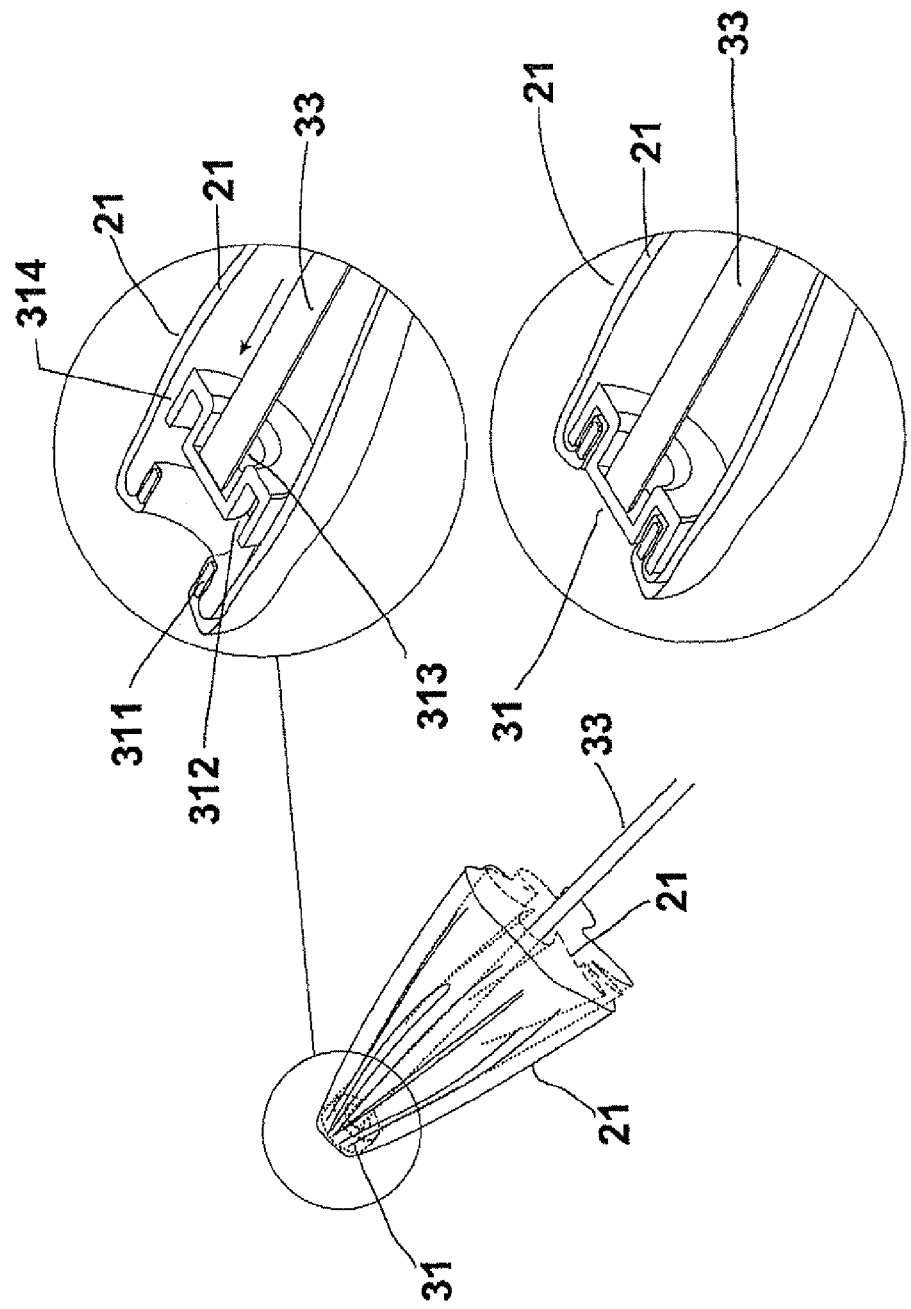
Figure 3I:
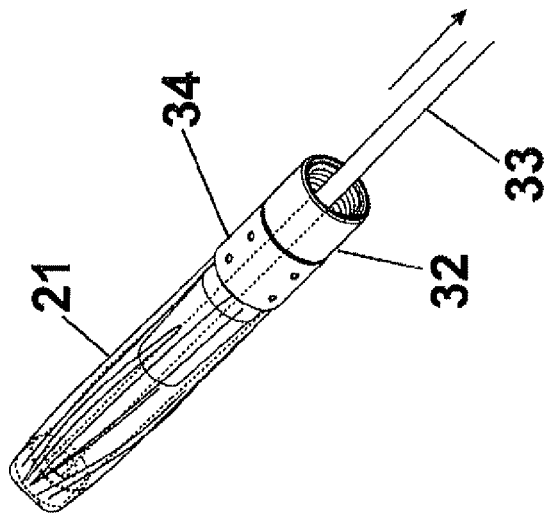
Figure 3H:
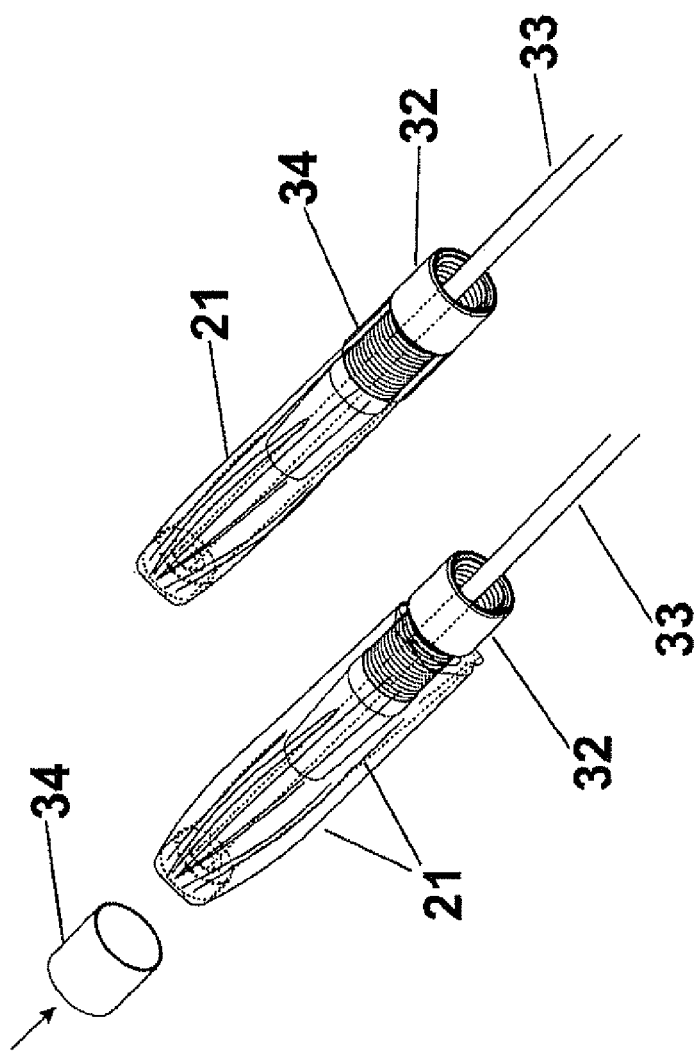
Figure 3J:
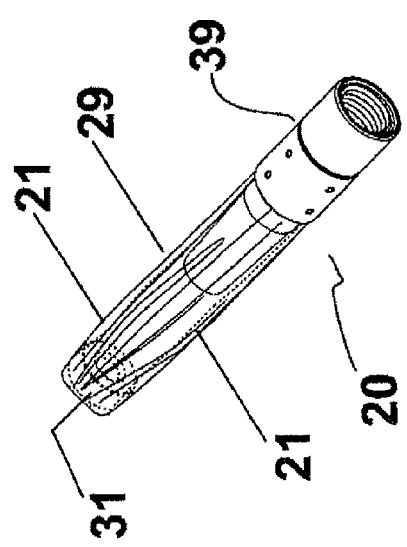

As shown in FIGS. 3a to 3c, a tubular surrounding wall 21 having a plurality of through holes 211 is inserted into a ring 311 and is folded so that two layers of flexible surrounding walls 21 are formed with the ring 311 imbedded between the two layers of flexible surrounding walls 21. The through holes 211 enable the internal surface and the external surface of the flexible container 29 surrounded by the surrounding walls 21 to communicate with each other. As shown in FIGS. 3d to 3e, the thrust part 31 comprises a receiving seat 314 and the ring 311, said receiving seat 314 comprising a central bore 313 and an annular groove 312 surrounding the central bore 314 and opposite to the central bore 314. The ring 311 with the two layers of flexible surrounding walls 21 are tightly received in the annular groove 312 of the receiving seat 314 and detained therein with the help from a thrust pin 33 pushing the central bore 313. As shown in FIGS. 3f to 3i, the tubular fitting 39 comprises a tubular nozzle 32 and a retainer ring 34, and the nozzle 32 is slidably received in the thrust pin 33 with opening-end portions of the two layers of flexible surrounding walls 21 wrapped around the nozzle 32 and the retainer ring 34 is mounted onto the nozzle 32 with the opening-end portions of the two layers of flexible surrounding walls 21 sandwiched by the retainer ring 34 and the nozzle 32. The retainer ring 34 is fixedly connected to the nozzle 32 by forming indentions. After removing the thrust pin 33 in a direction as indicated by the arrow shown in FIG. 3i, the medical implant 20 of the present invention is formed as shown in FIG. 3j.

The medical implant 20 is provided with threads 35 on the inner wall of the nozzle 32, which are threadably connected to corresponding threads 411 formed at one end of the infusion tube 41 with the thrust pin 33 received therein, as shown in FIGS. 4a and 4b.

As shown in FIGS. 4c to 4e, the medical implant 20 is connected to the infusion tube 41 of the medical kit 10 with the thrust pin 33 pushing the thrust part 31, so that the surrounding walls 21 of the medical implant 20 is tensioned into a linear shape, and thus the medical implant 20 can resist a counter force when a force is applied to insert the medical implant 20 into a pre-formed channel in a vertebral body 70 without the need of pre-twisting the medical implant 20 into a force-receiving shape in advance. The medical implant 20 is pushed into the pre-formed channel of the vertebral body 70 until the thrust part 31 hits the bottom of the pre-formed channel, the medical filling material 50 in a slurry form is then directly injected into the medical implant 20 to expand the surrounding walls 21 through the infusion tube 41. The medical implant 20 does not have a wrapping-deploying mechanism and does not require a retreat to be expanded in the vertebral body 70.

Figure 5A:
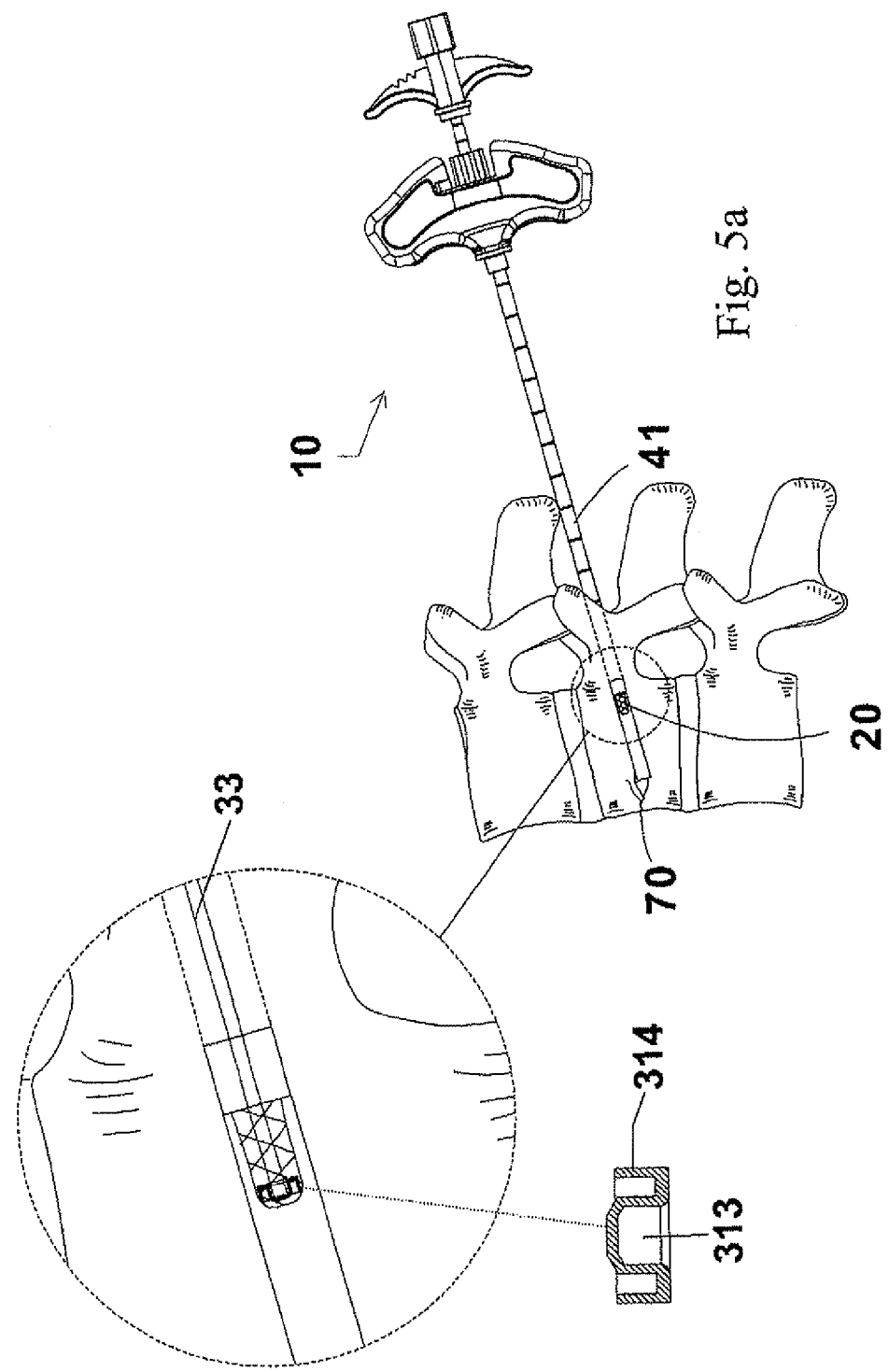
FIGS. 5a to 5b are schematic diagrams showing operation procedures for implanting the medical implant of the present invention into a vertebral body by using a medical kit of the present invention.
Figure 5B:
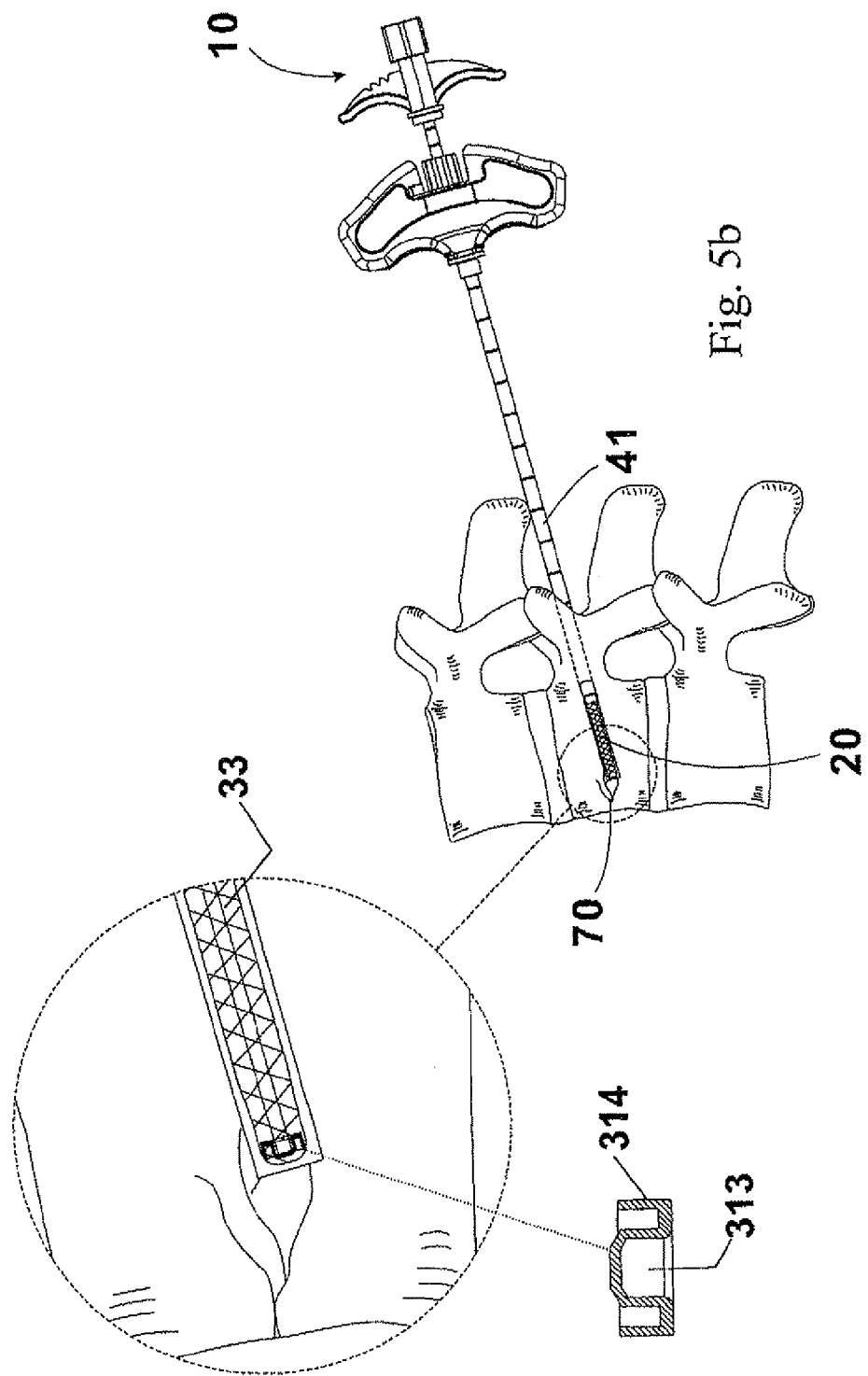

Referring to FIG. 5a and FIG. 5b, the operator can directly insert the medical implant 20 of the flexible non-airtight medical filling device 10 into the vertebral body 70 by using the infusion tube 41 and the thrust pin 33 received therein. The thrust pin 33 is pushed against the receiving seat 314 with one end of the thrust pin 33 well received in the central bore 313 of the receiving seat 314, so that the medical implant 20 is able to be pushed into a pre-form channel in the vertebral body 70 with the flexible surrounding walls of the medical implant 20 being tensioned.

The medical implant 20 is able to be expanded by the slurry medical filling material and expanded in the vertebral body 70. Furthermore, under the restriction of the flexible non-airtight surrounding walls of the medical implant 20, the slurry medical filling material is able to be hardened in the medical implant 20. The medical implant 20 with the medical filling material hardened therein will then be left in the vertebral body by threadably disconnecting the infusion tube 41.

The invention claimed is:

1. A medical implant comprising:
a flexible container, a proximal end thereof being an open end, said flexible container having 2n layers of flexible surrounding walls, each surrounding wall being provided with a plurality of through holes thereon through which an interior of the flexible container is in fluid communication with an exterior of the flexible container, wherein n is an integer of 1-5;
a tubular fitting being connected to the open end of the flexible container for inserting or infusing a medical filling material into the flexible container through the tubular fitting; and
a thrust part connected to the flexible surrounding walls of the flexible container and at a distal end of the flexible container,
wherein the thrust part comprises a receiving seat and a ring, said receiving seat comprising a blind central bore extending into the receiving seat from a proximal surface of the receiving seat and an annular groove extending into the receiving seat from a distal surface of the receiving seat and surrounding the blind central bore,
wherein n layer of a tubular surrounding wall is inserted into the ring and is folded so that the 2n layers of flexible surrounding walls are formed with the ring imbedded between the 2n layers of flexible surrounding walls, and the ring with the 2n layers of flexible surrounding walls are tightly received in the annular groove and detained therein, wherein n is defined as above.

2. The implant as claimed in claim 1, in which n is 1.

3. The implant as claimed in claim 2, in which the through holes have a size smaller than that of a mesh number of 100.

4. The implant as claimed in claim 2, in which the tubular fitting is provided with threads at a proximal end thereof for the convenience of mounting and dismounting of a tool for infusing the medical filling material.

5. The implant as claimed in claim 2, wherein the tubular fitting comprises a tubular nozzle and a retainer ring, and opening-end portions of the two layers of flexible surrounding walls wrapped around the nozzle and the retainer ring is mounted onto the tubular nozzle with the opening-end portions of the two layers of flexible surrounding walls sandwiched by the retainer ring and the nozzle.

6. A medical kit comprising a medical implant and an infusion tool, said implant comprising:
a flexible container, a proximal end thereof being an open end, said flexible container having 2n layers of flexible surrounding walls, each surrounding wall being provided with a plurality of through holes thereon through which an interior of the flexible container is in fluid communication with an exterior of the flexible container, wherein n is an integer of 1-5;
a tubular fitting being connected to the open end of the flexible container for inserting or infusing a medical filling material into the flexible container through the tubular fitting; and
a thrust part connected to the flexible surrounding walls of the flexible container and at a distal end of the flexible container,
wherein the thrust part comprises a receiving seat and a ring, said receiving seat comprising a blind central bore and an annular groove surrounding the blind central bore and opposite to the blind central bore,
wherein n layer of tubular surrounding wall is inserted into the ring and is folded so that the 2n layers of flexible surrounding walls are formed with the ring imbedded between the 2n layers of flexible surrounding walls, and the ring with the 2n layers of flexible surrounding walls are tightly received in the annular groove and detained therein, wherein n is defined as above; and
said infusion tool comprising:
an infusion tube; and
a syringe,
in which one end of the infusion tube is provided with external threads which are threadably connected to inner threads provided at a proximal end of the tubular fitting, and another end of the infusion tube is connected to said syringe, so that the infusion tube and the flexible container are in fluid communication with each other, and so that a medical filling material as a slurry in the syringe can be pushed and squeezed into the flexible container.

7. The medical kit as claimed in claim 6 further comprising a thrust pin adapted to be received in the flexible container and the tubular fitting, in which a distal end of the thrust pin is adapted to be received in the central bore of the receiving seat of the thrust part to tension the flexible surrounding walls of the flexible container.

8. A medical implant comprising:
a flexible container, a proximal end thereof being an open end, said flexible container having 2n layers of flexible surrounding walls, each surrounding wall being provided with a plurality of through holes thereon through which an interior of the flexible container is in fluid communication with an exterior of the flexible container;
a tubular fitting being connected to the open end of the flexible container for inserting or infusing a medical filling material into the flexible container through the tubular fitting; and
a thrust part connected to the flexible surrounding walls of the flexible container and at a distal end of the flexible container,
wherein:
the thrust part comprises a receiving seat and a ring, said receiving seat comprising a blind central bore and an annular groove surrounding the blind central bore and opposite to the blind central bore;
n layer of a tubular surrounding wall is inserted into the ring and is folded so that the 2n layers of flexible surrounding walls are formed with the ring imbedded between the 2n layers of flexible surrounding walls, and the ring with the 2n layers of flexible surrounding walls are tightly received in the annular groove and detained therein, wherein n is 1; and
the tubular fitting is provided with threads at a proximal end thereof for the convenience of mounting and dismounting of a tool for infusing the medical filling material.

9. A medical implant comprising:
a flexible container, a proximal end thereof being an open end, said flexible container having 2n layers of flexible surrounding walls, each surrounding wall being provided with a plurality of through holes thereon through which an interior of the flexible container is in fluid communication with an exterior of the flexible container;
a tubular fitting being connected to the open end of the flexible container for inserting or infusing a medical filling material into the flexible container through the tubular fitting; and
a thrust part connected to the flexible surrounding walls of the flexible container and at a distal end of the flexible container,
wherein the thrust part comprises a receiving seat and a ring, said receiving seat comprising a blind central bore and an annular groove surrounding the blind central bore and opposite to the blind central bore,
wherein:
n layer of a tubular surrounding wall is inserted into the ring and is folded so that the 2n layers of flexible surrounding walls are formed with the ring imbedded between the 2n layers of flexible surrounding walls, and the ring with the 2n layers of flexible surrounding walls are tightly received in the annular groove and detained therein, wherein n is 1; and
the tubular fitting comprises a tubular nozzle and a retainer ring, and opening-end portions of the two layers of flexible surrounding walls wrapped around the nozzle and the retainer ring is mounted onto the tubular nozzle with the opening-end portions of the two layers of flexible surrounding walls sandwiched by the retainer ring and the nozzle.

* * * * *